United States Patent [19]
Macor et al.

[11] Patent Number: 6,054,464
[45] Date of Patent: Apr. 25, 2000

[54] AZABICYCLIC ESTERS OF CARBAMIC ACIDS USEFUL IN THERAPY

[75] Inventors: John Macor, Penfield; Edwin Wu, Rochester, both of N.Y.

[73] Assignee: Astra Aktiebolag, Sodertalje, Sweden

[21] Appl. No.: 09/276,689

[22] Filed: Mar. 26, 1999

Related U.S. Application Data

[63] Continuation of application No. 08/836,143, Jun. 13, 1997.

[30] Foreign Application Priority Data

Feb. 23, 1996 [SE] Sweden .................................. 9600683

[51] Int. Cl.$^7$ ........................ A61K 31/395; C07D 221/02
[52] U.S. Cl. ........................... 514/299; 548/112; 548/512
[58] Field of Search .................................. 514/305, 413, 514/299; 546/137, 112; 548/512

[56] References Cited

U.S. PATENT DOCUMENTS 5,468,875  11/1995  Sabb et al. .............................. 548/512

FOREIGN PATENT DOCUMENTS 0 497 303    8/1992   European Pat. Off. .
38 39 385 A1 of 0000  Germany .

OTHER PUBLICATIONS

Brioni et al, "In Vivo' Profile of Novel Nicotinic Ligands . . . ," Med. Chem. Res, pp. 487–510 (1996).
Williams et al, "Neuronal Nicotinic Acetylcholine Receptors," DN&P, vol. 7, No. 4 pp. 205–223 (1994).
Janson et al, "Protective effects of chronic nicotine treatment . . . ," Progress in Brain Researh, vol. 79, pp 257–265 (1989).
Fagerstrom et al, "Nicotine may relieve symptoms of Parkinson's disease," Psychopharmacology, vol. 116, pp. 117–119 (1994).
Danysz et al, "Glutamate in CNS Disorders," DN&P, vol. 8, No. 5 pp. 261–277 (1995).
Donnelly–Roberts et al, "In vitro neuroprotective properties of the novel . . . ," Brain Research, vol. 719, pp. 36–44 (1996).
Shytle et al, "Transdermal Nicotine for Tourette's Syndrome," Drug Development Research, vol. 38, pp. 290–298 (1996).
Messi et al, "Activation of $\alpha_7$ nicotinic acetylcholine . . . ," FEBS Letters 411, pp. 32–38 (1997).
Oda et al, "Immunohistochemical study on choline acetyltransferase . . . ," Pathology International, vol. 45, pp. 933–939 (1995).
Virgo et al, "Characterisation of the distribution of choline . . . ," Journal of the Neurological Sciences, vol. 112, pp. 126–132 (1992).
O'Hara et al, "Nicotine and Nicotinic Receptors in the Circadian System," Psycholneuroendocrinology, vol. 23, No. 2, pp. 161–173 (1998).

(List continued on next page.)

Primary Examiner—John Kight
Assistant Examiner—Charanjit S. Aulakh
Attorney, Agent, or Firm—Nixon & Vanderhye

[57] ABSTRACT

A compound of formula

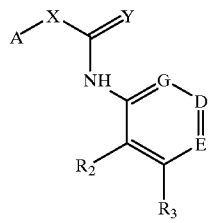

wherein:
A is

X is O or S; Y is O or S;

G and D are independently nitrogen or carbon with the proviso that no more than one of G, D, or E is nitrogen; E is N or C—$R_4$; $R_1$ is hydrogen or methyl; $R_2$ is hydrogen or fluoro; $R_3$ is hydrogen, halogen, $C_1$ to $C_3$ alkyl, —$OR_5$, —CN, —$CONH_2$, —$CO_2R_5$, —$NR_5R_6$ or phenyl optionally substituted with one to three of the following substituents: halogen, $C_1$ to $C_3$ alkyl, —$NO_2$, —CN, or —$OCH_3$; $R_4$ is hydrogen, halogen, $C_1$ to $C_3$ alkyl, —$OR_5$, —CN, —$CONH_2$, —$CO_2R_5$, —$NR_5R_6$ or phenyl optionally substituted with one to three of the following substituents: halogen, $C_1$ to $C_3$ alkyl, —$NO_2$, —CN, or —$OCH_3$;

or $R_2$ and $R_3$ or $R_3$ and $R_4$ may together represent a fused phenyl ring optionally substituted with one or two of the following substituents: halogen, $C_1$ to $C_3$ alkyl, —$NO_2$, —CN, or —$OCH_3$; $R_5$ and $R_6$ are independently hydrogen or $C_1$ to $C_3$ alkyl;

or an enantiomer thereof, and pharmaceutically acceptable salts thereof, processes for preparing the, compositions containing them, and their use in therapy, especially in the treatment or prophylaxis of psychotic disorders and intellectual impairment disorders, as well as intermediates and use of intermediates in synthesis.

3 Claims, No Drawings

OTHER PUBLICATIONS

Morley et al, "Light–Dark Variation in Response to Chronic Nicotine Treatment," Pharmacology Biochemistry & Behavior, vol. 37, pp. 239–245 (1990).

Bannon et al, "Broad–Spectrum, Non–Opioid Analgesic Activity . . . ," Science, vol. 279, pp. 77–91 (1998).

Khan et al, "Nociceptive and antinociceptive responses in intrathecally administered . . . ," Neuropharmacology, vol. 37, pp. 1515–1525 (1998).

Pullan et al, "Transdermal Nicotine for Active . . . ," The New England Journal of Medicine, vol. 330, No. 12, pp. 811–815 (1994).

Van Dijk et al, "Nicotine inhibits cytokine synthesis by mouse colonic mucosa," European Journal of Pharamacology, vol. 278, pp. R11–R12 (1995).

Dahlbom et al, "Studies on carbanilic acid esters of cyclic amino alcohols," Acta Pharm. Suecica, vol. 7, pp. 239–246 (1970).

Dahlbom et al, "3,4,5–trimethoxphenyl–carbamic acid esters of some cyclic amino alcohols . . . ," Acta Pharm. Suecica, vol. 4, pp. 211–216 (1970).

Gregan et al, "Synthesis and local anaesthetic activities of 3–(2–alkoxyphenylcarbamoyloxy) chinuclidinium chlorides," Pharmazie, vol. 48, pp. 465–466 (1993).

Chemical Abstracts, vol. 124, No. 5, Abstr. No. 55799b (1996).

Chemical Abstracts, vol. 108, No. 17, Abstr. No. 150772r (1988).

AZABICYCLIC ESTERS OF CARBAMIC ACIDS USEFUL IN THERAPY

This is a continuation of application Ser. No. 08/836,143, filed Jun. 13, 1997, now allowed.

FIELD OF THE INVENTION

This invention relates to novel azabicyclic esters of carbamic acids or pharmaceutically acceptable salts thereof, processes for preparing the, pharmaceutical compositions containing them and their use in therapy. A further object is to provide active compounds which are potent ligands for nicotinic acetylcholine receptors (nAChR's).

BACKGROUND OF THE INVENTION

The use of compounds which bind nicotinic acetylcholine receptors in the treatment of a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease has been discussed in "Nicotinic Acetylcholine Receptors: Molecular Biology, Chemistry, and Pharmacology", Chapter 5 in Annual Reports in Medicinal Chemistry, Volume 30, pp. 41–50, Academic Press Inc., San Diego, Calif. (1995) and in "Neuronal Nicotinic Acetylcholine Receptors," Drug News & Perspectives, Volume 7, pp. 205–223 (1994).

U.S. Pat. No. 5,468,875 discloses N-alkylcarbamic acid 1-azabicyclo[2.2.2]hept-3-yl esters which are centrally active muscarinic agents useful in the treatment of Alzheimer's disease and other disorders.

N-(2-Alkoxyphenyl)carbamic acid 1-azabicyclo[2.2.2]octan-3-yl esters are disclosed in *Pharmazie*, 48, 465–466 (1993) along with their local anaesthetic activity.

N-Phenylcarbamic acid 1-azabicyclo[2.2.2]octan-3-yl esters substituted at the ortho position on the phenyl ring are described as local anaesthetics in *Acta Pharma. Suecica*, 7, 239–246 (1970).

DISCLOSURE OF THE INVENTION

According to the invention we provide a compound of formula

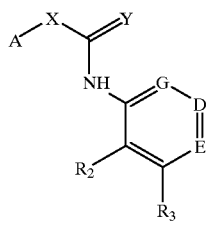

wherein:
A is

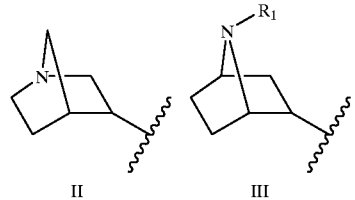

-continued

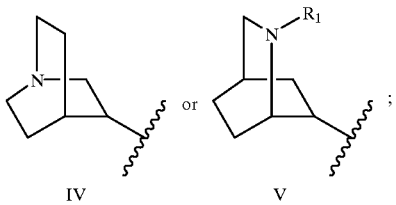

X is O or S;
Y is O or S;
G and D are independently nitrogen or carbon with the proviso that no more than one of G, D, or E is nitrogen;
E is N or C—$R_4$;
$R_1$ is hydrogen or methyl;
$R_2$ is hydrogen or fluoro;
$R_3$ is hydrogen, halogen, $C_1$ to $C_3$ alkyl, —$OR_5$, —CN, —$CONH_2$, —$CO_2R_5$, —$NR_5R_6$ or phenyl optionally substituted with one to three of the following substituents: halogen, $C_1$ to $C_3$ alkyl, —$NO_2$, —CN, or —$OCH_3$;
$R_4$ is hydrogen, halogen, $C_1$ to $C_3$ alkyl, —$OR_5$, —CN, —$CONH_2$, —$CO_2R_5$, —$NR_5R_6$ or phenyl optionally substituted with one to three of the following substituents: halogen, $C_1$ to $C_3$ alkyl, —$NO_2$, —CN, or —$OCH_3$;
or $R_2$ and $R_3$ or $R_3$ and $R_4$ may together represent a fused phenyl ring optionally substituted with one or two of the following substituents: halogen, $C_1$ to $C_3$ alkyl, —$NO_2$, —CN, or —$OCH_3$;
$R_5$ and $R_6$ are independently hydrogen or $C_1$ to $C_3$ alkyl;
or an enantiomer thereof, and pharmaceutically acceptable salts thereof.

The compounds of formula I are potent ligands for nicotinic acetylcholine receptors.

Unless otherwise indicated, the term "$C_1$–$C_3$ alkyl" referred to herein denotes a straight or branched chain alkyl group having from 1 to 3 carbon atoms or a cyclic alkyl group having 3 carbon atoms. Examples of such groups are methyl, ethyl, n-propyl, i-propyl and cyclopropyl.

Unless otherwise indicated, the term "halogen" referred to herein denotes fluoro, chloro, bromo or iodo.

Preferred compounds of the invention are compounds of formula I wherein A is formula II or IV; $R_2$ is hydrogen; X and Y are oxygen and G, D, and E are carbon.

Particularly preferred compounds of the invention include the following:
N-phenylcarbamic acid 1-azabicyclo[2.2.2]octan-3-yl ester;
N-(4-bromophenyl)carbamic acid 1-azabicyclo[2.2.2]octan-3-yl ester;
N-(4-methylphenyl)carbamic acid 1-azabicyclo[2.2.2]octan-3-yl ester;
N-(4-methoxyphenyl)carbamic acid 1-azabicyclo[2.2.2]octan-3-yl ester;
N-(3,4-dichlorophenyl)carbamic acid 1-azabicyclo[2.2.2]octan-3-yl ester;
N-(4-cyanophenyl)carbamic acid 1-azabicyclo[2.2.2]octan-3-yl ester;
N-phenylcarbamic acid 1-azabicyclo[2.2.2]heptan-3-yl ester;
N-(3-methoxyphenyl)carbamic acid 1-azabicyclo[2.2.2]octan-3-yl ester;
N-phenylthiocarbamic acid 1-azabicyclo[2.2.2]octan-3-yl ester;
N-(2-pyridyl)carbamic acid 1-azabicyclo[2.2.2]octan-3-yl ester;

N-(1-naphthyl)carbamic acid 1-azabicyclo[2.2.2]octan-3-yl ester;
N-phenylcarbamic acid (3R)-1-azabicyclo[2.2.2]octan-3-yl ester;
N-phenylcarbamic acid (3S)-1-azabicyclo[2.2.2]octan-3-yl ester;
N-(4-pyridyl)carbamic acid 1-azabicyclo[2.2.2]octan-3-yl ester;
N-(m-biphenyl)carbamic acid 1-azabicyclo[2.2.2]octan-3-yl ester;
N-(3-quinolinyl)carbamic acid 1-azabicyclo[2.2.2]octan-3-yl ester;

More particularly preferred compounds of the invention include the following:
N-(4-bromophenyl)carbamic acid 1-azabicyclo[2.2.2]octan-3-yl ester;
N-(4-methylphenyl)carbamic acid 1-azabicyclo[2.2.2]octan-3-yl ester;
N-(3,4-dichlorophenyl)carbamic acid 1-azabicyclo[2.2.2]octan-3-yl ester;
N-(m-biphenyl)carbamic acid 1-azabicyclo[2.2.2]octan-3-yl ester.

Other compounds of the invention include:
N-(2-fluorophenyl)carbamic acid 1-azabicyclo[2.2.2]octan-3-yl ester;
N-(3-fluorophenyl)carbamic acid 1-azabicyclo[2.2.2]octan-3-yl ester;
N-(4-fluorophenyl)carbamic acid 1-azabicyclo[2.2.2]octan-3-yl ester;
N-(4-chlorophenyl)carbamic acid 1-azabicyclo[2.2.2]octan-3-yl ester;
N-(3-chlorophenyl)carbamic acid 1-azabicyclo[2.2.2]octan-3-yl ester;
N-(3-bromophenyl)carbamic acid 1-azabicyclo[2.2.2]octan-3-yl ester;
N-(3-chloro-4-fluorophenyl)carbamic acid 1-azabicyclo[2.2.2]octan-3-yl ester;
N-(4-chloro-3-fluorophenyl)carbamic acid 1-azabicyclo[2.2.2]octan-3-yl ester.

According to the invention, we further provide a process for the preparation of compounds of formula I, and enantiomers thereof and pharmaceutically acceptable salts thereof.

Methods of Preparation

The compounds of formula I may be prepared according to the methods of Scheme 1, Scheme 2, and Scheme 3. In the reaction schemes and text that follow A, X, Y, G, D, E, $R_1$, $R_2$, $R_3$, $R_4$, $R_5$, and $R_6$, unless otherwise indicated, are as defined above for formula I.

Method a)

Scheme 1

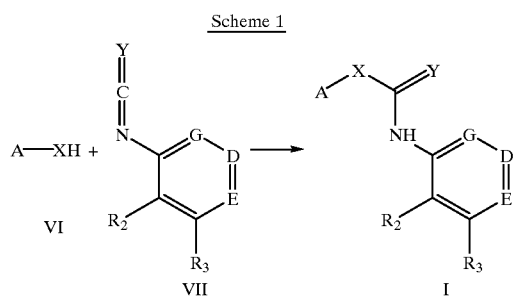

Compounds of formula I may be prepared from the condensation of a compound of the formula VI with an isocyanate or isothiocyanate of the formula VII in an inert solvent in the presence of a catalyst. Suitable inert solvents include ethers, for example, diethyl ether, tetrahydrofuran or dioxane; acetonitrile, toluene, N,N-dimethylformamide, and N-methylpyrrolidin-2-one. Preferably the solvent is acetonitrile, Suitable catalysts include tertiary amines such as trialkylamines, for example, triethylamine; 1,8-diazabicyclo[5.4.0]undec-7-ene (DBU), and 1,5-diazabicyclo[4.3.0]non-5-ene (DBN), preferably triethylamine, or dibutyltin dilaurate. The reaction is usually conducted at a temperature from about 25° C. to about 154° C., preferably about 25° C. to about 85° C. and at a pressure of about one to about three atmospheres, preferably at ambient pressure (about one atmosphere).

Method b)

Alternatively, a compound of formula I can be prepared according to Scheme 2.

Scheme 2

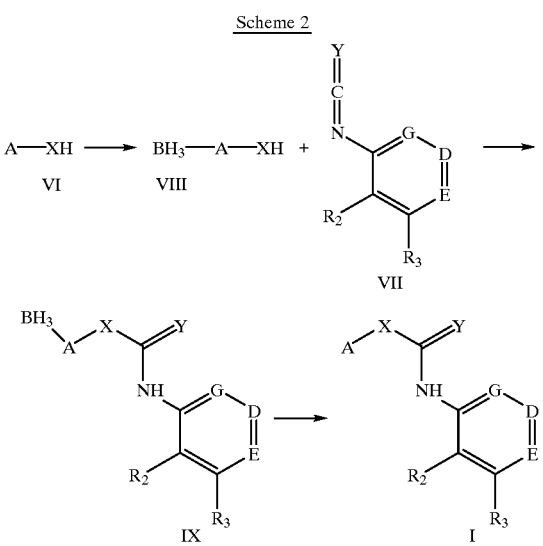

A compound of formula I may be prepared from a compound of formula IX via removal of the borane complex in a compound of formula IX using acid in an inert solvent. Suitable acids include mineral acids, for example, hydrochloric and hydrobromic acid; preferably hydrochloric acid. Suitable inert solvents include $C_1$ to $C_4$ alcohols and acetone; preferably acetone. The reaction is usually conducted at a temperature of about −10° C. to about 50° C., preferably at about 0° C. to about 25° C.

Compounds of formula IX are novel and can be prepared from the condensation of a compound of the formula VIII with an isocyanate or isothiocyanate of the formula VII in an inert solvent in the presence of a catalyst. Suitable inert solvents and catalysts, and reaction conditions are the same as described under method (a) above, for the condensation of the compound of formula VI with the compound of formula VII.

Compounds of formula VIII, which is the borane complex of a compound of formula VI, are novel and may be prepared via the treatment of a compound of formula VI with an equimolar amount of borane in tetrahydrofuran at about −10° C. to about 25° C., preferably at about 0° C. Extractive work up affords a compound of formula VIII which is generally used directly in the next step of the reaction sequence.

Compounds of formula VIII may be used as starting material in condensation reactions as well as starting material in a synthesis of a ligand for nicotinic acetylcholine receptors.

Method c)

Alternatively, compounds of formula I can be prepared as outlined in Scheme 3.

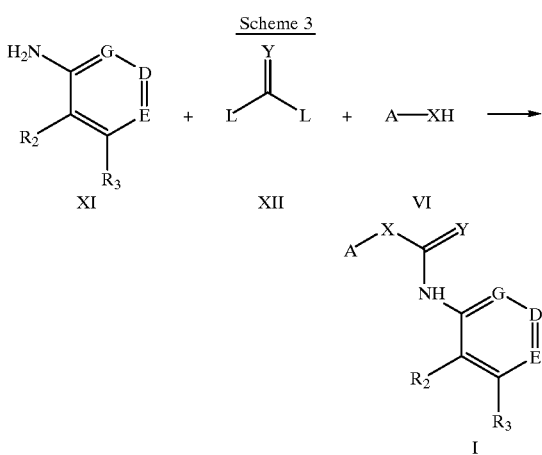

Scheme 3

A compound of formula I may be prepared from the sequential reaction of a compound of formula XI with a carbonyl donating compound of formula XII, wherein Y is as defined above and L is a leaving group, for example, chloride or imidazole, followed by immediate reaction of the resulting mixture with a compound of formula VI all done in the presence of a basic catalyst in an inert solvent. The preferred compound of formula XII is carbonyldiimidazole. Suitable bases include trialkylamines, for example, triethylamine; 1,8-diazabicyclo[5.4.0]undec-7-ene (DBU), and 1,5-diazabicyclo[4.3.0]non-5-ene (DBN); preferably triethylamine. Suitable inert solvents include N,N-dimethylformamide, acetonitrile, ethers, for example, tetrahydrofuran and dioxane, and acetone; preferably acetonitrile. The reaction is usually conducted at a temperature from about 25° C. to about 154° C., preferably about 25° C. to about 85° C. and at a pressure of about one to about three atmospheres, preferably at ambient pressure (about one atmosphere).

Compounds of formulae VI, VII, XI and XII are either commercially available or may be prepared by methods known to one skilled in the art.

The compounds of the invention and intermediates may be isolated from their reaction mixtures, and, if necessary, be further purified using standard techniques.

Acid addition salts of the compounds of formula I which may be mentioned include salts of mineral acids, for example, the hydrochloride and hydrobromide salts; and salts formed with organic acids such as formate, acetate, maleate, benzoate and fumarate salts.

Acid addition salts of compounds of formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuum or by freeze drying. The reaction may be a metathetical process or it may be carried out on an ion exchange resin.

The compounds of formula I exist in tautomeric or enantiomeric forms, all of which are included within the scope of the invention. The various optical isomers may be isolated by separation of a racemic mixture of the compounds using conventional techniques, for example, fractional crystallization or chiral HPLC. Alternatively the individual enantiomers may be made by reaction of the appropriate optically active starting materials under reaction conditions which will not cause racemization.

Intermediate compounds also exist in enantiomeric forms and may be used as purified enantiomers, racemates or mixtures.

Utility

The compounds of formula I are agonists of nicotinic acetylcholine receptors ["Nicotinic Acetylcholine Receptors: Molecular Biology, Chemistry, and Pharmacology", Chapter 5 in Annual Reports in Medicinal Chemistry, Volume 30, pp. 41–50, Academic Press Inc., San Diego, Calif. (1995)]. While not being limited by theory, it is believed that agonists of the α7 nAChR (nicotinic acetylcholine receptor) subtype should be useful in the treatment or prophylaxis of psychotic disorders and intellectual impairment disorders, and have advantages over compounds which are, or are also, agonists of the α4 nAChR subtype. Therefore, compounds which are selective for the α7 nAChR subtype are preferred. The compounds of the invention are indicated as pharmaceuticals, in particular in the treatment or prophylaxis of psychotic disorders and intellectual impairment disorders. Examples of psychotic disorders include schizophrenia, mania, manic depression and anxiety. Examples of intellectual impairment disorders include Alzheimer's disease, learning deficit, cognition deficit, attention deficit, memory loss, autism and Attention Deficit Hyperactivity Disorder. The compounds of the invention may also be useful as analgesics in the treatment of pain (including chronic pain) and in the treatment or prophylaxis of Parkinson's disease, Huntington's disease, Tourette's syndrome, Amyotrophic Lateral Sclerosis and neurodegenerative disorders in which there is dysfunction of the cholinergic system. The compounds may further be indicated for the treatment or prophylaxis of jetlag, for use in inducing the cessation of smoking, and for the treatment or prophylaxis of nicotine addiction (including that resulting from exposure to products containing nicotine).

It is also believed that compounds of formula I may be useful in the treatment and prophylaxis of inflammatory bowel diseases, for example, ulcerative colitis.

Thus, according to a further aspect of the invention we provide a compound of formula I, or an enantiomer thereof, or a pharmaceutically acceptable salt thereof, for use as a pharmaceutical.

According to another aspect of the invention is the use of a compound of formula I, an enantiomer thereof or a pharmaceutically acceptable salt thereof, in the manufacture of a medicament for the treatment or prophylaxis of one of the above mentioned diseases or conditions; and a method of treatment or prophylaxis of one of the above mentioned diseases or conditions, which comprises administering a therapeutically effective amount of a compound of formula I, or an enantiomer thereof or a pharmaceutically acceptable salt thereof, to a person suffering from or susceptible to such a disease or condition.

For the above-mentioned therapeutic uses the dosage administered will, of course, vary with the compound employed, the mode of administration and the treatment desired. However, in general, satisfactory results are obtained when the compounds of the invention are administered at a daily dosage of from about 0.1 mg to about 20 mg per kg of animal body weight, preferably given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound optionally admixed with a solid or liquid pharmaceutical carrier or diluent.

Pharmaceutical compositions

The compounds of formula I and enantiomers thereof and pharmaceutically acceptable salts thereof may be used on their own, or in the form or appropriate medicinal compositions. Administration may be by, but is not limited to, enteral (including oral, sublingual or rectal), intranasal, topical or parenteral routes. Conventional procedures for the selection and preparation of suitable pharmaceutical compositions are described in, for example, "Pharmaceuticals—The Science of Dosage Form Designs", M. E. Aulton, Churchill Livingstone, 1988.

According to the invention, there is provided a pharmaceutical composition for treating or preventing a condition or disorder as exemplified above arising from dysfunction of nicotinic acetylcholine receptor neurotransmission in a mammal, preferably a human, comprising an amount of a compound of formula I, an enantiomer thereof or a pharmaceutically acceptable salt thereof, effective in treating or preventing such disorder or condition and optionally an inert pharmaceutically acceptable carrier.

According to a further aspect of the invention, there is provided a pharmaceutical composition including preferably less than 80% by weight and more preferably less than 50% by weight of a compound of the invention optionally in admixture with an inert pharmaceutically acceptable diluent or carrier.

Examples of diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal, administration include tablets, capsules, syrups and dragees; sustained release compositions include those in which the active ingredient is bound to an ion exchange resin which is optionally coated with a diffusion barrier to modify the release properties of the resin.

There is also provided a process for the preparation of such a pharmaceutical composition which comprises mixing the ingredients.

Pharmacology

The pharmacological activity of the compounds of the invention may be measured in the tests set out below:

Test A—Assay for affinity to the α7 nAChR subtype $[^{125}I]$-α-Bungarotoxin (BTX) binding to rat hippocampal membranes Rat hippocampi were homogenized in 20 volumes of cold homogenization buffer (HB: concentrations of constituents (mM): tris(hydroxymethyl)aminomethane 50; MgCl$_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12000 g, washed, and resuspended in HB. Membranes (30–80 μg) were incubated with 5 mM $[^{125}I]$-α-BTX, 1 mg/mL BSA (bovine serum albumin), test drug, and either 2 mM CaCl$_2$ or 0.5 mM EGTA [ethylene glycol-bis(β-aminoethyl) ether] for 2 hours at 21° C., and then filtered and washed 4 times over Whatman glass fibre filters (thickness C) using a Brandel cell harvester. Pretreating the filters for 3 hours with 1% (BSA/0.01% PEI (polyethyleneimine) in water was critical for low filter blanks (0.07% of total counts per minute). Nonspecific binding was described by 100 μM (−)-nicotine, and specific binding was typically 75%.

Test B—Assay for affinity to the α4 nAChR subtype $[^3H]$-(−)-Nicotine binding.

Using a procedure modified from Martino-Barrows and Kellar, *Mol. Pharma.*, 31, 169–174, (1987), the contents of which are hereby incorporated herein by reference, rat brain (cortex and hippocampus) was homogenized as in the $[^{125}I]$-α-BTX binding assay, centrifuged for 20 minutes at 12000 g, washed twice, and then resuspended in HB containing 100 μM diisopropyl fluorophosphate. After 20 minutes at 4° C., membranes (approximately 0.5 mg) were incubated with 3 nM $[^3H]$-(−)-nicotine, test drug, 1 μM atropine, and either 2 mM CaCl$_2$ or 0.5 mM EGTA for 1 hour at 4° C., and then filtered over Whatman glass fibre filters (thickness B) (pretreated for 1 hour with 0.5% PEI) using a Brandel cell harvester. Nonspecific binding was described by 100 μM carbachol, and specific binding was typically 84%.

Binding data analysis for Tests A and B

IC$_{50}$ values and pseudo Hill coefficients (n$_H$) were calculated using the non-linear curve fitting program ALLFIT [A. DeLean, P. J. Munson and D. Rodbard, *Am J. Physiol.*, 235, E97-E102 (1977)]. Saturation curves were fitted to a one site model, using the non-linear regression program ENZFITTER [R. J. Leatherbarrow (1987)], yielding K$_D$ values of 1.67 and 1.70 nM for the $[^{125}I]$-α-BTX and $[^3H]$-(−)-nicotine ligands respectively. K$_i$ values were estimated using the general Cheng-Prustoff equation:

$$K_i = [IC_{50}]/((2+([\text{ligand}]/[K_D])^n)^{1/n}-1)$$

where a value of n=1 was used whenever n$_H$<1.5 and a value n=2 was used when n$_H$≥1.5. Samples were assayed in triplicate and reproducibility was typically ±5%. K$_i$ values were determined using 6 or more drug concentrations. The compounds of the invention are compounds with binding affinities (K$_i$) of less than 1000 nM in either Test A or Test B, indicating that they are expected to have useful therapeutic activity.

When compared with other compounds, the compounds of the invention have the advantage that they may be less toxic, be more efficacious, be longer acting, have a broader range of activity, be more potent, be more selective for the α7 nAChR subtype, produce fewer side effects, are more easily absorbed or have other useful pharmacological properties.

Experimental part

The following Examples illustrate the preparation of compounds of the present invention but in no way limit the scope of the invention.

General Experimental Procedures

Commercial reagents were used without further purification. NMR data are reported in parts per million (δ), and are referenced to the chemical shift of tetramethylsilane or the deuterium lock from the sample solvent, and were obtained on either a Bruker 250 MHz or Bruker 500 MHz instrument. Chromatography (silica gel filtration) utilized 230–400 mesh silica gel. Room temperature refers to 20–25° C.

EXAMPLE 1

General Synthesis of N-Arylcarbamic acid esters, N-Heteroarylcarbamic acid esters, N-Arylthiocarbamic acid esters and N-Heteroarylthiocarbamic acid esters A mixture of the azabicycloalkyl alcohol (formula VI, 2.00 mmol), the appropriate isocyanate or isothiocyanate (formula VII, 2.00 mmol), triethylamine (20 mol %), and acetonitrile (10 mL) was heated at reflux under nitrogen for 2 to 8 hours, unless otherwise noted. Then, absolute methanol (0.10 mL, 2.5 mmol) was added, and reflux was continued for 1 hour. The resulting reaction solution was cooled to room temperature, and any precipitated solid was isolated via filtration. If the solid was not the pure carbamic acid ester, additional purification could be achieved by recrystallization or column chromatography using silica gel (approximately 50 g) and elution with 9:1:0.1 methylene chloride/methanol/ammonium hydroxide to afford the pure carbamic acid ester.

Following this procedure the following compounds were prepared:

A. N-(4-Bromophenyl)carbamic acid 1-azabicyclo[2.2.2]octan-3-yl ester

3-Quinuclidinol and 4-bromophenyl isocyanate were used. Filtration of the precipitated solid from the cooled reaction mixture afforded the title compound (60%) as a white solid: mp 217.5–219.5° C.; FAB LRMS $^m$/z (relative intensity, %) 328 (16), 327 ([MH$^+$ with Br$^{81}$], 100), 326 (16), 325 ([MH$^+$ with Br$^{79}$], 100).

B. N-(4-Methylphenyl)carbamic acid 1-azabicyclo[2.2.2]octan-3-yl ester

3-Quinuclidinol and 4-tolyl isocyanate were used. Filtration of the precipitated solid from the cooled reaction mixture afforded the title compound (93%) as a white solid: mp 186.0–187.5° C.; FAB LRMS $^m$/z (relative intensity, %) 262 (21), 261 ([MH$^+$], 100).

C. N-(3,4-Dichlorophenyl)carbamic acid 1-azabicyclo[2.2.2]octan-3yl ester

3-Quinuclidinol and 3,4-dichlorophenyl isocyanate were used. Filtration of the precipitated solid from the cooled reaction mixture afforded the title compound (60%) as a white solid: mp 181.0–184.0° C.; FAB LRMS $^m$/z (relative intensity, %) 319 ([MH$^+$ with two Cl$^{37}$], 13), 318 (11), 317 ([MH$^+$ with one Cl$^{37}$], 71), 316 (18), 315 ([MH$^+$ with two Cl$^{35}$], 100).

D. N-(4-Methoxyphenyl)carbamic acid 1-azabicyclo[2.2.2]octan-3yl ester

3-Quinuclidinol and 4-methoxyphenyl isocyanate were used. The solid which precipitated from the reaction mixture was recrystallized from ethyl acetate to afford the title compound (43%) as a white solid: mp 159.5–160.5° C.; FAB LRMS $^m$/z (relative intensity, %) 277 (MH$^+$1, 16), 110 (100).

E. N-(2-Fluorophenyl)carbamic acid 1-azabicyclo[2.2.2]octan-3-yl ester

3-Quinuclidinol and 2-fluorophenyl isocyanate were used. The reaction solution was evaporated under reduced pressure, and the residual solid was recrystallized from ethyl acetate to afford the title compound (79%) as a white solid: mp 124.0–126.0° C.; FAB LRMS $^m$/z (relative intensity %) 265 (MH$^+$, 22), 110 (100).

F. N-(3-Methoxyphenyl)carbamic acid 1-azabicyclo[2.2.2]octan-3-yl ester

3-Quinuclidinol and 3-methoxyphenyl isocyanate were used. The reaction solution was evaporated under reduced pressure, and the residual solid was recrystallized from ethyl acetate to afford the title compound (60%) as a white solid: mp 130.5–132.0° C.; FAB LRMS $^m$/z (relative intensity, %) 278 (18), 277 (MH$^+$, 100).

G. N-Phenylthiocarbamic acid 1-azabicyclo[2.2.2]octan-3-yl ester

3-Quinuclidinol and phenyl isothiocyanate were used. The reaction solution was heated at reflux under nitrogen for 6 days. The reaction solution was chromatographed using silica gel and elution with 10% methanol in methylene chloride followed by a solution of methylene chloride/methanol/ammonium hydroxide (9:1:0.1) to afford a white foam. This foam was dissolved in ethyl acetate/ether (1:9, 10 mL/g of foam), and the resulting cloudy solution was filtered through diatomaceous earth. The resultant filtrate was evaporated under reduced pressure, and the residual foam was crystallized from ethyl acetate/hexanes (1:3) to afford the title compound (29%) as a white solid: mp 132.0–133.0° C.; FAB LRMS $^m$/z (relative intensity, %) 263 (MH$^+$, 14), 110 (100).

EXAMPLE 2

General Synthesis of N-Arylcarbamic acid esters, N-Heteroarylcarbamic acid esters, N-Arylthiocarbamic acid esters and N-Heteroarylthiocarbamic acid esters.

To a stirred solution of the appropriate aniline (formula XI, 10.00 mmol) and triethylamine (20 mol %) in anhydrous acetonitrile (50 mL) was added carbonyldiimidazole (1.622 g, 10.00 mmol), and the resulting reaction mixture was stirred at room temperature under nitrogen overnight (16 hours). Then, an alcohol of formula VI (10.00 mmol) was added, and the resulting reaction mixture was heated at reflux under nitrogen for 48 hours. The resulting reaction mixture was evaporated under reduced pressure, and the residue was partitioned between ethyl acetate (150 mL) and saturated aqueous sodium carbonate (150 mL). The aqueous layer was removed, and the ethyl acetate layer was washed with a saturated aqueous sodium carbonate solution (4×100 mL). The ethyl acetate layer was dried (MgSO$_4$), and evaporated under reduced pressure. The residue was chromatographed using 5 to 20% methanol saturated with ammonia in chloroform to afford the title compound. If necessary, recrystallization can provide more pure title compound.

Following this procedure the following compounds were prepared:

A. N-(4-Cyanophenyl)carbamic acid 1-azabicyclo[2.2.2]octan-3-yl ester

3-Quinuclidinol and 4-aminobenzonitrile were used. Chromatography afforded a residue which was triturated in ethyl acetate to afford the title compound (11%) as a white solid: mp 180.0–182.0° C.; FAB LRMS $^m$/z (relative intensity, %) 273 (17), 272 (MH$^+$, 100), 110 (52).

B. N-(2-Pyridyl)carbamic acid 1-azabicyclo[2.2.2]octan-3-yl ester

3-Quinuclidinol and 2-aminopyridine were used. The title compound was isolated as a white solid (8%): mp 166–167° C.; FAB LRMS $^m$z 248 (MH$^+$).

EXAMPLE 3

General Synthesis of N-Arylcarbamic acid 1-azabicyclo[2.2.2]heptan-3-yl esters and N-Arylcarbamic acid 1-azabicyclo[2.2.2]octan-3-yl esters To an ice cold suspension of the appropriate azabicycloalkyl alcohol (formula VI, 13.3 mmol) in tetrahydrofuran (15 mL) was dropwise added over 30 minutes borane-tetrahydrofuran complex (1.0M in THF, 13.3 mL, 13.3 mmol). The resulting solution was warmed up to room temperature for 1 hour. A few drops of water were added followed by brine solution (30 mL) and ethyl acetate (30 mL). the organic layer was separated, the aqueous layer extracted with ethyl acetate (30 mL), and the combined extracts were dried (MgSO$_4$) and evaporated under reduced pressure to give a borane complex of the appropriate azabicycloalkyl alcohol. A solution of the borane complex (2.48 mmol), an aryl isocyanate (formula VII, 3.0 mmol), and triethylamine (0.1 mL) in anhydrous tetrahydrofuran (5 mL) was stirred under nitrogen at room temperature for 24 hours and then evaporated under reduced pressure. The residue was treated with acetone (5 mL) and 2.5N HCl (3 mL) and stirred at room temperature overnight. The mixture was then evaporated under reduced pressure, and the resulting residue was further purified as required.

Following this procedure the following compounds were prepared:

A. N-Phenylcarbamic acid 1-azabicyclo[2.2.1]heptan-3-yl ester

1-Azabicyclo[2.2.1]heptan-3-endo-ol [*Helv. Chim Acta,* 75, 507 (1992]and phenyl isocyanate were used. The residual solid resulting from the above described procedure was recrystallized twice from isopropanol to afford the title compound (56%) as a white crystalline solid: FAB LRMS $^m/z$ (relative intensity, %) 233 ([MH$^+$], 100). Anal. calcd. for $C_{13}H_{17}N_2O_2Cl$: C, 58.10; H, 6.37; N, 10.42. Found C, 58.11; H, 6.40; N, 10.42%.

B. N-Phenylcarbamic acid 1-azabicyclo[2.2.2]octan-3-yl ester

1-Azabicyclo[2.2.2]octan-3-ol and phenyl isocyanate were used. The residual solid resulting from the above described procedure was purified via column chromatography eluting with a 1:10 ratio of methanol:chloroform to afford the title compound (86%) as a white solid: NMR (CDCl$_3$) δ7.60–7.0 (m, 5H, Ph), 4.81 (m, 1H, CH—OCO), 3.27 (m, 1H, one of NCH$_2$C—O), 2.9 (m, 5H, N(CH$_2$)$_2$ and one of NCH$_2$C—O), 2.1 (m, 1H, methine at C$_4$), 2.05–1.30 (m, 4H, CH$_2$ at C$_5$ and C$_8$); FAB LRMS $^m/z$ (relative intensity, %) 247 ([MH$^+$], 100).

C. N-(1-Naphthyl)carbamic acid 1-azabicyclo[2.2.2]octan-3-yl ester

1-Naphthylisocyanate and 3-quinuclidinol were used. The title compound was isolated as a white solid (34%): mp 186–188° C.; FAB LRMS $^m/z$ 297 (MH$^+$).

EXAMPLE 4

N-Phenylcarbamic acid (3R)-1-azabicyclo[2.2.2]octan-3-yl ester

A solution of (3R)-(−)-quinuclidin-3-ol (0.30 g, 2.36 mmol) [M. Langlois, C. Meyr, and J. L. Soulier, *Synth. Comm.,* 23, 1895–1911 (1992)], triethylamine (0.07 mL, 20 mol %) and phenyl isocyanate (0.28 mL, 2.58 mmol, 1.1 equivalents) in anhydrous acetonitrile (5 mL) was heated at reflux under nitrogen for 46 hours. Water (25 mL) was added, and the resulting aqueous mixture was extracted with ethyl acetate (2×25 mL). The resulting extracts were combined, dried (MgSO$_4$), and evaporated under reduced pressure. The resulting foam was crystallized using ethyl acetate/hexanes (2:1) to afford a white solid (0.42 g). this white solid was placed in 1N HCl (20 mL), and the resulting aqueous mixture was extracted with ethyl acetate (2×25 mL). These organic extracts were discarded. The aqueous solution was made basic (pH>13) with solid Na$_2$CO$_3$ and aqueous 10% KOH. The resulting aqueous solution was extracted with ethyl acetate (2×25 mL), and these extracts were combined, dried (MgSO$_4$), and evaporated under reduced pressure. The resulting solid was triturated in ether/hexanes (3:1) to afford the title compound (0.100 g, 17%) as a white, crystalline solid: mp 131.0–132.0° C.; FAB LRMS $^m/z$ (relative intensity, %) 247 (MH$^+$, 41), 110 (100); $[\alpha]^{22}_D$=+7.5° (c=0.9, MeOH).

EXAMPLE 5

N-Phenylcarbamic acid (3S)-1-azabicyclo[2.2.2]octan-3-yl ester

A solution of (3S-(+)-quinuclidin-3-ol (0.50 g, 3.93 mmol) [M. Langlois, C. Meyer, and J. L. Soulier, *Synth. Comm.,* 23, 1895–1911 (1992)], phenyl isocyanate (0.47 mL, 4.32 mmol, 1.1 equivalents), and dibutyltin dilaurate (0.013 mL, 0.08 mmol) in anhydrous toluene (20 mL) was heated at reflux under nitrogen for 1 hour. The resulting reaction mixture was evaporated under reduced pressure, and the resulting solid was placed in 1N HCl (25 mL). The resulting aqueous mixture was extracted with ethyl acetate (2×25 mL), basified to pH 10 with Na$_2$CO$_3$, and extracted with chloroform (3×50 mL). The chloroform extracts were combined, dried (MgSO$_4$), and evaporated under reduced pressure. The resulting solid was recrystallized using toluene (5 mL) to afford the title compound (0.875 g, 90%) as a white solid: mp 129.0–130.0° C.; FAB LRMS $^m/z$ (relative intensity, %) 247 (MH$^+$, 39), 110 (100); $[\alpha]^{22}_D$=−7.5° (c=1.0, MeOH).

EXAMPLE 6

N-(4-Pyridyl)carbamic acid 1-azabicyclo[2.2.2]octan-3-yl ester

3-Quinuclidinol and 4-(2,6-dicloropyridyl)isocyanate were used to synthesis N-[4-(2,6-dichloropyridyl)]carbamic acid 1-azabicyclo[2.2.2]octan-3-yl ester following the method described in Example 3. A solution of N-[4-(2,6-dichloropyridyl)]carbamic acid 1-azabicyclo[2.2.2]octan-3-yl ester (0.5 g, 1.58 mmol), palladium chloride (0.3 g) and potassium acetate (0.32 g) in methanol (10 mL) was shaken under a hydrogen atmosphere (3 atm). The reaction mixture was filtered, and the filtrate was evaporated under reduced pressure. The residue was partitioned between chloroform and saturated sodium carbonate and separated. The aqueous layer was further extracted with chloroform. The chloroform extracts were combined, dried (MgSO$_4$) and evaporated to give a solid. This solid was triturated in ether to afford the title compound (69%) as a solid: mp 149–151° C.; FAB LRMS $^m/z$ 248 (MH$^+$).

EXAMPLE 7

General Method for Preparing N-Arylcarbamic acid esters and N-Heteroarylcarbamic acid esters To a stirred solution of 3-quinuclidinol (10 mmol) in anhydrous chloroform (40 mL) and at 0° C. was added 1.93M phosgene in toluene (5.2 mL, 10 mmol) under nitrogen, and the resulting mixture was stirred at 0° C. for 1 hour to give a very fine suspension. The appropriate arylamine or heteroarylamine (10 mmol) was then added, followed by triethylamine (11 mmol). The cooling bath was removed 30 minutes later and the resulting reaction mixture was stirred at room temperature overnight. Chloroform (40 mL) was added to the reaction mixture followed by saturated aqueous sodium bicarbonate until the mixture was basic. The chloroform layer was separated. The aqueous layer was further extracted with chloroform (30 mL). The organic layers were combined, dried (MgSO$_4$) and evaporated under reduced pressure. The residue was purified by column chromatography eluting with 3 to 5% methanol saturated with ammonia in chloroform to give the pure carbamic acid ester.

Following this procedure the following compounds were synthesized:

A. N-(m-Biphenyl)carbamic acid 1-Azabicyclo[2.2.2]octan-3-yl ester

3-Quinuclidinol and m-aminobiphenyl were used to give the title compound (26%) as white crystals: mp 203–204.5° C.; FAB LRMS $^m/z$ 323 (MH$^+$).

B. N-(3-Quinolinyl)carbamic acid 1-azabicyclo[2.2.2]octan-3yl ester

3-Quinuclidinol and 3-aminoquinoline were used to give the title compound (46%) as a solid: mp 135–137° C.; FAB LRMS $m/z$ 298 (MH$^+$).

What is claimed is:

1. A method of treatment or prophylaxis of Parkinson's disease, Huntington's disease, Tourette's syndrome, Amyotropic Lateral Sclerosis or neurodegenerative disorders in which there is dysfunction of the cholinergic system, which comprises administering a therapeutically effective amount of a compound of formula

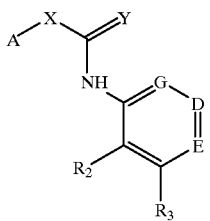

I wherein:

A is

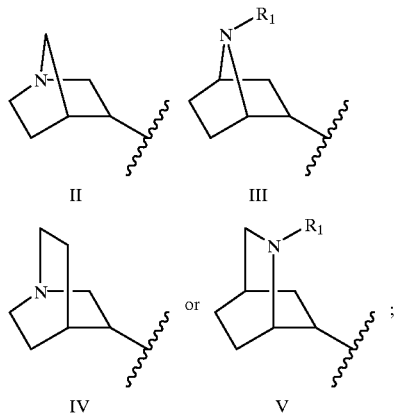

X is O or S;

Y is O or S;

G and D are independently nitrogen or carbon with the proviso that no more than one of G, D, or E is nitrogen;

E is N or C—R$_4$;

R$_1$ is hydrogen or methyl;

R$_2$ is hydrogen or fluoro;

R$_3$ is hydrogen, halogen, C$_1$ to C$_3$ alkyl, —OR$_5$, —CN, —CONH$_2$, —CO$_2$R$_5$, —NR$_5$R$_6$ or phenyl optionally substituted with one to three of the following substituents: halogen, C$_1$ to C$_3$ alkyl, —NO$_2$, —CH, or —OCH$_3$;

R$_4$ is hydrogen, halogen, C$_1$ to C$_3$ alkyl, —OR$_5$, —CN, —CONH$_2$, —CO$_2$R$_5$, —NR$_5$R$_6$ or phenyl optionally substituted with one to three of the following substituents: halogen, C$_1$ to C$_3$ alkyl, —NO$_2$, —CN, or —OCH$_3$;

or R$_2$ and R$_3$ or R$_3$ and R$_4$ may together represent a fused phenyl ring optionally substituted with one or two of the following substituents: halogen, C$_1$ to C$_3$ alkyl, —NO$_2$, —CN, or —OCH$_3$;

R$_5$ and R$_6$ are independently hydrogen or C$_1$ to C$_3$ alkyl;

or an enantiomer thereof, or a pharmaceutically acceptable salt thereof.

2. A method of treatment or prophylaxis of jetlag, cessation of smoking, nicotine addition including that resulting from exposure to products containing nicotine, pain, and inflammatory bowel diseases which comprises administering a therapeutically effective amount of a compound of formula

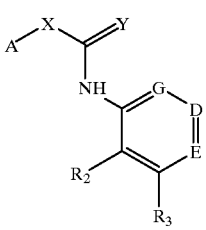

I wherein:

A is

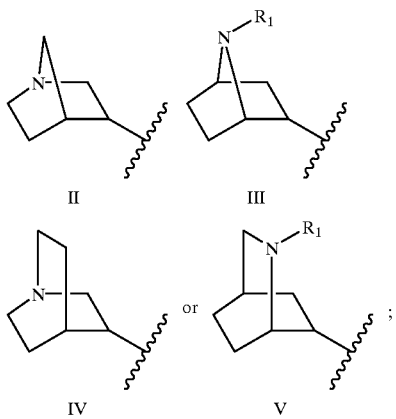

X is O or S;

Y is O or S;

G and D are independently nitrogen or carbon with the proviso that no more than one of G, D, or E is nitrogen;

E is N or C—R$_4$;

R$_1$ is hydrogen or methyl;

R$_2$ is hydrogen or fluoro;

R$_3$ is hydrogen, halogen, C$_1$ to C$_3$ alkyl, —OR$_5$, —CN, —CONH$_2$, —CO$_2$R$_5$, —NR$_5$R$_6$ or phenyl optionally substituted with one to three of the following substituents: halogen, C$_1$ to C$_3$ alkyl, —NO$_2$, —CN, or —OCH$_3$;

R$_4$ is hydrogen, halogen, C$_1$ to C$_3$ alkyl, —OR$_5$, —CN, —CONH$_2$, —CO$_2$R$_5$, —NR$_5$R$_6$ or phenyl optionally substituted with one to three of the following substituents: halogen, C$_1$ to C$_3$ alkyl, —NO$_2$, —CN, or —OCH$_3$;

or R$_2$ and R$_3$ or R$_3$ and R$_4$ may together represent a fused phenyl ring optionally substituted with one or two of the following substituents: halogen, C$_1$ to C$_3$ alkyl, —NO$_2$, —CN, or —OCH$_3$;

R$_5$ and R$_6$ are independently hydrogen or C$_1$ to C$_3$ alkyl;

or an enantiomer thereof, or a pharmaceutically acceptable salt thereof.

3. A compound of formula IX

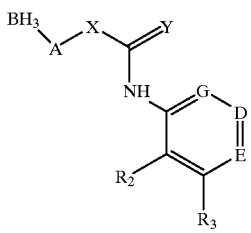

wherein

A is

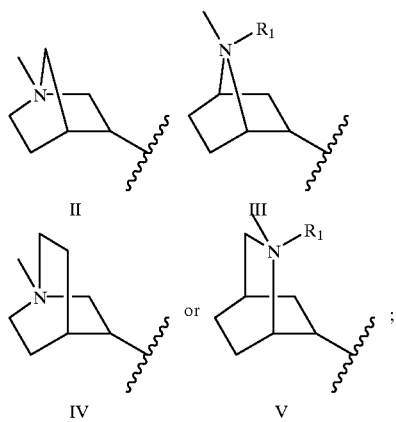

X is O or S;

Y is O or S;

G and D are independently nitrogen or carbon with the proviso that no more than one of G, D, or E is nitrogen;

E is N or C—$R_4$;

$R_1$ is hydrogen or methyl;

$R_2$ is hydrogen or fluoro;

$R_3$ is hydrogen, halogen, $C_1$ to $C_3$ alkyl, —$OR_5$, —CN, —$CONH_2$, —$CO_2R_5$, —$NR_5R_6$ or phenyl optionally substituted with one to three of the following substituents: halogen, $C_1$ to $C_3$ alkyl, —$NO_2$, —CN, or —$OCH_3$;

$R_4$ is hydrogen, halogen, $C_1$ to $C_3$ alkyl, —$OR_5$, —CN, —$CONH_2$, —$CO_2R_5$, —$NR_5R_6$ or phenyl optionally substituted with one to three of the following substituents: halogen, $C_1$ to $C_3$ alkyl, —$NO_2$, —CN, or —$OCH_3$;

or $R_2$ and $R_3$ or $R_3$ and $R_4$ may together represent a fused phenyl ring optionally substituted with one or two of the following substituents: halogen, $C_1$ $C_3$ alkyl, —$NO_2$, —CN, or —$OCH_3$;

$R_5$ and $R_6$ are independently hydrogen or $C_1$ to $C_3$ alkyl;

or an enantiomer thereof.

* * * * *